United States Patent [19]

Laanio et al.

[11] 4,190,433
[45] Feb. 26, 1980

[54] THIOESTER OF 1,2-DIPHENYL-CYCLOHEX-1-ENE-4-CARBOXYLIC-ACID

[75] Inventors: Verena Laanio, Arisdorf; Werner Föry, Basel; Rolf Schurter, Binningen, all of Switzerland

[73] Assignee: Ciba-Geigy Corporation, Ardsley, N.Y.

[21] Appl. No.: 918,210

[22] Filed: Jun. 22, 1978

Related U.S. Application Data

[63] Continuation-in-part of Ser. No. 713,477, Aug. 11, 1976, abandoned.

[30] Foreign Application Priority Data

Aug. 15, 1975 [CH] Switzerland ............. 01664/75
Aug. 15, 1975 [CH] Switzerland ............. 01665/75
Aug. 15, 1976 [CH] Switzerland ............. 01666/75

[51] Int. Cl.² .................... A01N 9/12; C07C 153/11
[52] U.S. Cl. ............................... 71/100; 71/76; 71/78; 260/455 R
[58] Field of Search .................. 71/100; 260/455 R

[56] References Cited

U.S. PATENT DOCUMENTS

| | | | |
|---|---|---|---|
| 2,631,935 | 3/1953 | Baumgartner | 71/100 |
| 2,901,498 | 8/1959 | Tilles et al. | 71/100 |
| 3,260,736 | 7/1966 | Martin et al. | 71/100 |
| 3,282,977 | 11/1966 | Barnas | 71/100 |
| 3,296,292 | 1/1967 | Richter et al. | 71/100 |
| 3,673,237 | 6/1972 | Janiak | 71/100 |

OTHER PUBLICATIONS

Alder et al., "Diene Synthesis With, etc.;" (1951), CA45, pp. 4684–4685, (1951).
Alder et al., "Diene Synthesis XXX, etc.;" (1950), CA46, pp. 3967–3969, (1950).

*Primary Examiner*—Glennon H. Hollrah
*Attorney, Agent, or Firm*—Frederick H. Rabin; Harry Falber

[57] ABSTRACT

Esters of 1,2-diphenyl-cyclohex-1-ene-4-thiocarboxylic-acid are effective plant growth regulating agents. They are useful for controlling wild oats in cereal cultures and for growth inhibition in different cultures, e.g. for the inhibition of suckers in tobacco plants.

3 Claims, No Drawings

THIOESTER OF 1,2-DIPHENYL-CYCLOHEX-1-ENE-4-CARBOXYLIC-ACID

CROSS REFERENCE TO RELATED APPLICATION

This is a continuation-in-part of our application, Ser. No. 713,477, filed Aug. 11, 1976, now abandoned.

This invention relates to new 1,2-diphenyl-cyclohex-1-ene-4-thiocarboxylic-acid-esters with plant-growth regulating activity, corresponding to the formula I

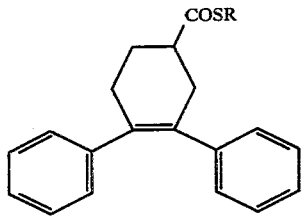

wherein R is $C_1$-$C_{12}$ alkyl, optionally substituted by chlorine $C_1$-$C_4$ alkoxy or $C_1$-$C_4$ alkoxycarbonyl, $C_3$-$C_6$ alkenyl or alkinyl, $C_3$-$C_6$ cycloalkyl or cycloalkenyl, phenyl or benzyl, optionally substituted by halogen, methyl, methoxy or methylthio.

In the above definitions, halogen denotes fluorine, chlorine, bromine or iodine. The alkyl, alkenyl or alkinyl radicals may be of straight chain or ramified and contain the given number of carbon atoms.

The 1,2-diphenyl-cyclohex-1-ene-4-carboxylic-acid, which may also be termed 3,4-diphenyl-$\Delta^3$-tetrahydrobenzoic acid, is known [Liebigs Ann. 570, 201 (1950)]. No mention is made in the literature of a plant-influencing activity. Such an activity becomes more evident when salt or ester formation occurs and particularly with the thioesters. Of special interest proved to be 1,2-diphenyl-cyclohex-1-ene-4-thiocarboxilic acid-alkyl esters, but especially the methyl ester (compound 1).

The invention also provides a process for the manufacture of the compounds of the formula I, which comprises reacting acrylonitrile, acrylic acid, or a derivative of acrylic acid of the formula II $$CH_2=CH-CO-OH \quad (II)$$

with optionally a diene of the formula III

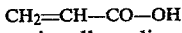

in a Diels-Alder reaction, or with a compound of the formula IIIa

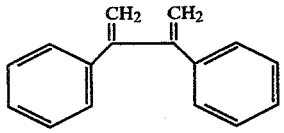

in a modified Diels-Alder reaction (Proc. Chem. Soc. 1963, 217), which is followed, if acrylic acid is used, by an esterification with a thiol R—SH or a reactive derivative thereof, to obtain corresponding thioesters, and, if acrylonitrile is used, initially by a saponification of the nitrile group to give the carboxyl group followed by optional esterification thereof.

The process of the invention is consequently a cyclisation reaction in the presence of a functional acid group, which in turn is either in the form of an acid or ester group, and which, if the acid is used, hat to be converted into the ester after the cyclisation is complete.

The cyclisation process of this invention is carried out at normal pressure or elevated pressure in the temperature range between 80° and 200° C., preferably between 120° and 150° C., in solvents which are suitable for Diels-Alder reactions, such as hydrocarbons (benzene, toluene, xylenes) [cf. H. Wollweber "Diels-Alder-Reaktionen", Georg Thieme Verlag, Stuttgart, 1972]. The process, however, can also be carried out in the absence of a solvent.

When using compound IIIa, the addition of dehydrating agents (splitting off of 2 moles of water) is necessary to form compound III as intermediate. It is possible to use conventional agents, such as $Al_2O_3$, p-toluenesulphonic acid, $KHSO_4$, acetic anhydride/sodium acetate etc., for the dehydration.

The starting products of the formulae III and IIIa are partly known compounds are they can be obtained by methods which are known per se, for example:

"Grignard" reacton of the corresponding benzile derivatives

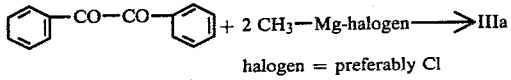

halogen = preferably Cl

[Bull. Soc. chim France 43, 873 (1928)]

Dimerisation of the corresponding acetophenone derivative (a) electrochemically, (b) by irradiation (h·v), (c) in the presence of aluminium powder

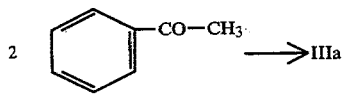

(a) [J. Am. Chem. Soc. 75, 5127 (1953)]
(b) [Tetrahedron 25, 4501 (1969)]
(c) [J. Org. Chem. 37, 2367 (1972)]

The following Example illustrates the process of the present invention including the manufacture of the starting products. The parts are parts by weight. Further compounds of the formula I which were obtained by the described process are listed in the subsequent table.

EXAMPLE (a) (1st method)

A mixture of 50 parts of 2,3-diphenyl-2,3-dihydroxybutane and 0.5 part of freshly dehydrated $KHSO_4$ is distilled for 50 minutes at 11 Torr and 200° C. bath temperature. The fraction which is collected within the boiling range of 150°–180° C./11 Torr yields 43.8 parts of crude 2,3-diphenyl-1,3-butadiene. The product is stirred direct with 21.5 parts of acrylic acid and 2 parts of hydroquinone under a nitrogen atmosphere for 3 hours at 130° to 140° C.

The cooled reaction product is treated with diethyl ether and extracted with 1 normal NaOH. The aqueous phase is acidified with concentrated hydrochloric acid and extracted with diethyl ether. The organic phase is dried over $Na_2SO_4$ and concentrated in vacuo to yield 21 parts of 3,4-diphenyl-$\Delta^3$-tetrahydrobenzoic acid with a melting point of 136°–140° C.

(b) (2nd method)

A mixture of 7.2 parts of 2,3-diphenyl-2,3-dihydroxybutane, 3.2 parts of acrylic acid, 0.1 parts of p-toluenesulphonic acid and 0.3 part of hydroquinone is dissolved in 12 parts of acetone and the solution is kept for 25 minutes in a Carius tube. The solution is concentrated in vacuo and the oily residue is worked up as described in (a) above to yield 2.2 parts of 3,4-diphenyl-$\Delta^3$-tetrahydrobenzoic acid with a melting point of 136°–140° C.

(c) 27.8 parts of 3,4-diphenyl-$\Delta^3$-tetrahydrobenzoic acid are suspended in a mixture of 60 parts by volume of abs. chloroform and 0.8 part of dimethyl formamide. Then 15.5 parts of thionyl chloride are added dropwise at 0° C. in the course of 5 minutes. The mixture is stirred at 0° C. for 15 minutes at room temperature and stirred for 20 minutes at 40° C. The clear, yellow solution is concentrated in vacuo and dried in a high vacuum at 50° C. to yield 29 g of 3,4-diphenyl-$\Delta^3$-tetrahydrobenzoyl chloride.

Boiling point: 160° C./0.005 Torr.

(d) 2.3 parts of 3,4-diphenyl-$\Delta^3$-tetrahydrobenzoyl chloride are dissolved in 20 parts by volume of abs. diethyl ether. At −5° C. to 0° C. and under a nitrogen atmosphere, a mixture of 0.95 part of benzylmercaptan and 0.6 part of abs. pyridine, dissolved in 10 parts by volume of ether, are added dropwise in the course of 10 minutes. The mixture is stirred for 30 minutes at 0° C. and for 30 minutes at room temperature. The reaction product is filtered and the filter residue is washed with ether. The combined filtrates are washed with cold water, dried and concentrated in vacuo.

Yield: 2.2 parts of S-benzyl-3,4-diphenyl-$\Delta^3$-tetrahydrobenzoate: $n_D^{20}$: 1.6099.

The following compounds of the formula I are obtained in this manner or by one of the methods indicated above:

| Compound | R | Physical constant |
|---|---|---|
| 1 | $CH_3$ | m.p. 73°–75° C. |
| 2 | $C_2H_5$ | |
| 3 | n-$C_3H_7$ | |
| 4 | iso$C_3H_7$ | $n_D^{25}$ 1.5911 |
| 5 | n-$C_4H_9$ | $n_D^{25}$ 1.5862 |
| 6 | sec.$C_4H_9$ | |
| 7 | iso.$C_4H_9$ | |
| 8 | n-$C_5H_{11}$ | |
| 9 | n-$C_8H_{17}$ | $n_D^{25}$ 1.5670 |
| 10 | n-$C_{12}H_{25}$ | |
| 11 | 2-methoxyethyl | |
| 12 | 2-n-butoxyethyl | |
| 13 | 1-ethoxycarbonylmethyl | |
| 14 | 3-phenylpropyl | $n_D^{25}$ 1.6052 |
| 15 | 2-propenyl | |
| 16 | cyclohexyl | m.p. 75°–77° C. |
| 17 | benzyl | $n_D^{25}$ 1.6099 |
| 18 | 4-chlorobenzyl | $n_D^{25}$ 1.6160 |
| 19 | 4-methoxybenzyl | |
| 20 | phenyl | m.p. 107°–108° C. |
| 21 | 4-fluorophenyl | |
| 22 | 4-bromo-3-methylphenyl | m.p. 86°–87° C. |
| 23 | 4-nitrophenyl | |
| 24 | 4-methoxyphenyl | |

The active substances of the present invention of the formula I, and the corresponding compositions which contain them, intervene in the physiological processes of plant development and can be used for various purposes in connection with the increase in yield, ease of harvesting and labour-saving in measures taken on cultivated plants. The various effects of these active substances depend substantially on the time of application (from the ripening stage of the plant) and on the concentrations employed. However, these effects are in turn different depending on the species of plant.

Compound structures of 4-phenyl-cyclohex-(3 or 4)-ene-1-carboxylates are disclosed within a substantial group of compounds in general form in German Offenlegungsschrift No. 1,900,658. Anti-fertility properties are ascribed to such compounds, which appear to make them suitable for rodent control. No particulars are given on effects on plants. That compounds of the formula I of the present invention act on plants is therefore completely surprising.

The active substance of this invention of the formula I, and the compositions which contain them, influence the plant growth. The supporting tissues of the stems of treated plants are strengthened. The formation of undesired suckers in various plant species, is very greatly diminished, and the vegetative growth of e.g. vines is inhibited.

By influencing the growth, the active substance used according to the invention can substantially increase the yield of plants (e.g. fruit, seeds, leaves). For example the vegetative growth of soya bean and other leguminous plants is reduced and the generative growth promoted, whereby a direct increase in the yield is achieved.

Special mention is also to be made of the possibility of inhibiting the growth of suckers in tobacco plants with the active substances of the present invention, when the leading shoot has been cut off shortly before flowering in order to bring about the desired increase in growth of the leaves.

The principal kind of plant regulation, however, resides in the special property of the compounds of the formula I to effect in specific weeds a growth inhibition so pronounced that it approximates to a herbicidal action and the compounds can be used in practice for this purpose. When applied to a large number of monocotyledonous and dicotyledonous weeds (Setaria, Alopecurus, Sinapis, Galium etc.), the compounds effect a stunted growth. From the point of view of maintaining cultivated land, this effect provides a particularly advantageous weed control to the extent that, independently of the growth of useful plants, a uniform, low plant cover is retained, which counteracts soil erosion by wind or water. The marked selective activity of the compounds of the formula I, which either has no effect on the important major crops, such as sugar beet, wheat, barley, rye and others, or even—as in types of cereals—increases the breaking strength of the plant through slight growth reduction, results in an economically very interesting method of protecting cultivations of plants from the spread of weeds. A particularly advantageous feature of the compounds of the formula I is the pronounced herbicidal-like growth inhibition of wild oats (*Avena fatua*), which are among the most important grass-like weeds in crops of useful plants, above all in cereals. Experience has shown wild oats to be among the most difficult weeds to control. They are controlled only imperfectly by a few herbicides, but not at all by the majority of commercially available herbicides.

The invention therefore provides simultaneously a method of controlling weeds in crops of useful plants by applying compounds of the formula I, which cause stunted growth or compositions which contain them.

Such a method of inhibiting plant growth does not bring about any change in the sense of a mutation in the life cycle of the plant which is determined by genetic characteristics.

The maintenance of pure grass cultivations, such as those in public parks and gardens, in urban areas, industrial sites, or along main roads, railway embankments or the embankments of water bodies, has to be considered in connection with the reduction in growth of grasses. In all such cases it is normally necessary to cut the turf or grass periodically. This operation is not only time-consuming, complicated and expensive in respect of labour and machinery, but involves the personnel concerned and road users in considerable hazard in the traffic sector.

For this reason there is therefore an urgent need in areas with extensive traffic networks on the one hand to maintain and care for the grassy covering necessary for strengthening road shoulders and embankments on traffic routes, and on the other hand to keep it at reasonable height by simple means during the entire vegetation period. This need is fulfilled in a very advantageous manner by applying the compounds of the formula I.

The active substances of the formula I can be applied to the surface to be treated simultaneously or successively with further active substances. These active substances can be both fertilisers, trace element agents or other preparations which influence plant growth. However, they can also be selective herbicides, insecticides, fungicides, bactericides, nematicides, molluscicides or mixtures of these preparations, if appropriate together with additional carriers or further additives which assist application.

Suitble carriers or additives may be solid or liquid and correspond to the substances conventionally used in the art of formulation, for example: natural and regenerated substances, solvents, dispersing agents, wetting agents, stickers, thickeners, binders or fertilizers.

For application, the compounds of formula I can be in the following application forms.

Solid preparations: dusts, tracking agents, granulates (coated granulates, impregnated granulates and homogranulates);
Liquid preparations:
 (a) water-dispersible active substance concentrates: wettable powders, pastes or emulsions;
 (b) solutions.

To these mixtures can also be added additives which stabilise the active substance and/or non-ionic, anionic and cationic substances, which for example improve the adhesion of the active ingredients on plants or parts of plants (stickers) and/or ensure a better wettability (wetting agents) and dispersibility (dispersing agents). Examples of suitable stickers are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products.

Water-dispersible concentrates of the active substance, i.e. wettable powders, pastes and emulsifiable concentrates, are compositions which can be diluted with water to any desired concentration. They consist of active substance, carrier, optionally additives which stabilise the active substance, surface-active substances and anti-foam agents and, optionally, solvents.

The content of active substance in the above described compositions is between 0.1 and 95%, preferably between 1 and 80%. Application forms can be diluted to as low a content of active substance as 0.001%. As a rule the rates of application are from 0.1 to 10 kg of active substance per hectare, preferably from 0.25 to 5 kg per hectare.

The active substances of formula I can be formulated for example in the following way:

Dusts

The following substances are used for the preparation of (a) a 5% (b) a 2% dust:

(a)
5 parts of active substance
95 parts of talcum (b)
2 parts of active substance
1 part of highly dispersed silicic acid
97 parts of talcum The active ingredients are mixted and ground with the carriers.

Granulate

The following substances are used to obtain a 5% granulate:

5 parts of active substance
0.25 parts of epichlorohydrin
0.25 parts of cetyl polyglycol ether
3.50 parts of polyethylene glycol
91 parts of kaolin (particle size 0.3–0.8 mm)

The active substance is mixed with epichlorohydrin and dissolved in 6 parts of acetone, then the polyethylene glycol and cetyl polyglycol ether are added. The resultant solution is sprayed onto kaolin and the acetone is subsequently evaporated in vacuo.

Wettable Powder

The following ingredients are used to prepare a 25% wettable powder.

25 parts of active substance,
4.5 parts of calcium lignin sulphonate,
1.9 parts of Champagne chalk/hydroxyethyl cellulose mixture (1:1),
1.5 parts of sodium dibutyl naphthalenesulphonate,
19.5 parts of silicic acid,
19.5 parts of Champagne chalk,
28.1 parts of kaolin;

The active substances are intimately mixed in suitable mixers with the additives, and the mixture is then milled in appropriate mills and rollers. Wettable powders are obtained which can be diluted with water to give suspensions of any desired concentration.

Emulsifiable concentrates

The following substances are used to produce a 25% emulsifiable concentrate:

250 parts of active substance
150 parts of a condensation product of 1 mole of tributylphenol and 10 moles of ethylene oxide as wetting agent. The preparation is bulked to a volume of 1000 ml with xylene.

By diluting such concentrates with water it is possible to obtain emulsions of any desired concentration which are suitable for application to plants to inhibit their growth. To illustrate the plant growth influencing properties of the compounds of the formula I, the herbicidal/growth-inhibiting activity was determined by means of the following tests.

Test A

Herbicidal post-emergence application

Weeds in the 2- to 6-leaf stage (or up to the tillering stage with grasses) which have been sown in pots and kept in a greenhouse are sprayed with an aqueous emulsion of active substance (obtained from a 25% emulsifiable concentrate) in rates of application of 0.5 to 4 kg of active substance per hectare. The plants are then kept at 20° to 24° C. and 45 to 60% relative humidity. The test is evaluated 25 days after treatment. The evaluation is made using the following linear rating:
9 = plants unaffected (controls)
1 = plants withered
8–2 = intermediate stages of activity
The evaluation of the test shows that the 1-methylthioester of 3,4-diphenyl-cyclohex-3-ene-1-carboxylic acid, effected a pronounced reduction in growth of Amaranthus, Sinapis, Ipomoea, Galium, Rumex and Setaria but chiefly of *Avena fatua*, whilst important plant crops, such as wheat, barley, maize, cultivated sorghum millet, rice, sugar beet and cotton were not injured. The vegetative growth of soya plants was inhibited, but otherwise their further development was normal.

Test B

Growth inhibition of grasses (post-emergence method)

Seeds of the grasses *Lolium perenne, Poa Pratensis, Festuca ovina* and *Dactylis glomerata* were sown in plastic dishes filled with an earth/turf/sand mixture and watered normally. Each week the emergent grasses were cut back to a height of 4 cm above the soil and then sprayed with aqueous spray broths of the active substances of the formula I 40 days after sowing and 1 day after the last cutting. The amount of active substance corresponded to a rate of application of 5 kg per hectare. The growth of the grasses was evaluated 10 and 21 days after application using the following linear scale rating:
1 = -pronounced inhibition (no further growth from the time of application)
9 = no inhibition (growth as untreated control)
The active substances of the formula I showed a marked growth inhibition (rating 1 to 4).

Test C

Inhibition of the growth of undesired suckers in tobacco plants

Tobacco of the variety "Xanthi" was reared in a greenhouse. The leading shoot was cut off shortly before flowering. One day later, 3 plants at a time were sprayed from above with 10 ml of an aqueous preparation of a compound of the formula I. The selected active substance concentrations corresponded to rates of application of 10 kg, 6 kg and 3 kg per hectare. The inhibiting action on the suckers of the 6 uppermost leaf axils was determined 14 days after application.

The compounds of the formula I effected prounced inhibition of the sucker growth even when used in low relates of application.

We claim:

1. The methyl ester of 1,2-diphenyl-cyclohex-1-ene-4-thiocarboxylic-acid.
2. A herbicidal composition comprising a herbicidally effective amount of a compound of claim 1 together with a suitable inert carrier therefor.
3. A method for controlling *Avena fatua* (wild oats) in cultures of cereal, which comprises applying to cereal fields infested with the weed avena fatua in post-emergence application an effective amount of an ester of claim 1.

* * * * *